United States Patent [19]
Irvine

[11] Patent Number: 5,191,129
[45] Date of Patent: Mar. 2, 1993

[54] METHOD OF PREPARING AN ISOPROPANOL AND DIISOPROPYL ETHER OXYGENATE MOTOR FUEL ADDITIVE

[75] Inventor: Robert L. Irvine, Overland Park, Kans.

[73] Assignee: The Pritchard Corporation, Overland Park, Kans.

[21] Appl. No.: 877,642

[22] Filed: May 1, 1992

[51] Int. Cl.⁵ .................. C07C 29/04; C07C 41/00
[52] U.S. Cl. ............................. 568/895; 568/694; 568/696; 568/899
[58] Field of Search ............ 568/850, 889, 671, 579, 568/581, 886, 895, 899, 695, 694, 696

[56] References Cited

U.S. PATENT DOCUMENTS

| | | | |
|---|---|---|---|
| 4,424,388 | 1/1984 | Braithwaite | 568/899 |
| 4,456,776 | 6/1984 | Neier et al. | 568/899 |
| 4,471,142 | 9/1984 | Burton et al. | 568/696 |
| 4,831,197 | 5/1989 | Henn et al. | 568/899 |

*Primary Examiner*—Werren B. Lone
*Attorney, Agent, or Firm*—Hovey, Williams, Timmons & Collins

[57] ABSTRACT

Propene is reacted with water in a multi-stage, fluidized bed catalytic reactor to produce an oxygenate motor fuel additive containing a major proportion of isopropanol (IPA), some diisopropyl ether (IPE) and some water. The molar ratio of water to propene introduced into each catalytic stage of the multi-stage reactor is maintained within a range of from about 2:1 to about 6:1. The temperature of the reactants in each of the catalytic stages is maintained within a range of from about 250° F. to about 300° F. and the pressure at a level of from about 1200 psia to about 3000 psia. The temperature in each catalytic stage increases from the initial catalytic stage to the final catalytic stage with the temperature increase being limited to a value within a range of from about 8° F. to about 2° F. The pressure of the final stage of the catalytic section is controlled so that the reaction product containing the organic constituents including oxygenates provides a concentrated, less dense liquid stream which may be easily separated from the aqueous liquid phase in the final stage. The liquid phase is recycled to the catalytic zone while unreacted propene is separated from the oxygenates. Some water is purposefully retained in the oxygenate to take advantage of the solubilization of the IPA component. Seasonal gasoline component specifications may be met by simply controlling the amount of water allowed to remain in the oxygenate product. Relatively small distillation towers are suitable in the present process because of the 92% conversion factor of the propene entering. Thus, only about ⅓rd of the quantity of unconverted hydrocarbons must be separated in the present process as compared with existing commercial methods for the same yield of motor fuel oxygenates.

22 Claims, 3 Drawing Sheets

METHOD OF PREPARING AN ISOPROPANOL AND DIISOPROPYL ETHER OXYGENATE MOTOR FUEL ADDITIVE

BACKGROUND OF THE INVENTION

1. Field of the Invention

This invention relates to an oxygenate additive for motor fuels and particularly to an additive containing a major proportion of isopropanol (IPA), some diisopropyl ether (IPE), and some water.

Recently enacted governmental regulations require that motor fuels such as gasoline be formulated in a manner to avoid production of certain noxious waste by-products discharged to the atmosphere when the fuel is burned in an engine. These regulations are directed toward the reduction of olefins and aromatics, and in order to implement such goal, require the presence of oxygen. In the United States, motor fuels for certain designated geographical areas must contain 2 weight percent (wt %) oxygen by Jan. 1, 1995 and 2.7 wt % oxygen by Nov. 1, 1992 in particular areas. Addition of oxygenates to gasoline is intended to reduce hydrocarbon and carbon monoxide exhaust emissions to a level which meets presently mandated emission standards.

2. Description of the Prior Art a. Motor Fuel Oxygenate Additives

Alcohols have long been added to motor fuels such as gasoline to increase the octane rating of the fuel. Ethanol and methanol have been the principal alcohols employed for this purpose. Methanol has now been excluded as an additive for gasoline because of the unacceptable emission products which result when burned in the presence of a hydrocarbon fuel.

Ethanol on the other hand has properties which limit its use as a motor fuel additive, particularly if employed at levels which are effective in reducing unburned hydrocarbon and carbon monoxide combustion by-products. Ethanol, which has been dehydrated to an extent that the cost of the product is low enough to permit economic use of the alcohol as a gasoline additive, still contains an amount of water that causes the alcohol to be immiscible in the fuel. As a result, the ethanol additive tends to separate from the hydrocarbon fuel under certain ambient temperature conditions. Furthermore, gasoline while stored can accumulate additional quantities of water from the atmosphere. This exposure of the gasoline to additional water, can trigger phase separation of the alcohol from the fuel.

A co-solvent is required to prevent phase separation of the $C_1$ and $C_2$ alcohols from the fuel. Tertiary butyl alcohol (TBA) is an example of a co-solvent that has been used with $C_1$ and $C_2$ additives for motor fuels.

Present oxygenates used as motor fuel additives include methyl tertiary butyl ether (MTBE), ethyl tertiary butyl ether (ETBE), and tertiary amyl methyl ether (TAME). These products proved to be expensive and required importation of methanol for production of MTBE and TAME, or ethanol for preparation of ETBE. Methanol or ethanol are not products which are conventionally produced in refinery processes, thus increasing the cost of the additive.

Isopropanol (IPA) has been proposed as an oxygenate additive for fuels, but available methods for preparation of IPA have limited its usefulness from a cost standpoint. Limited amounts of diisopropyl ether (IPE) removed from IPA during purification of the alcohol have found their way into motor fuels in Europe. IPE and IPA additions to the motor fuel though, were for deicing and dewatering purposes. In view of the fact that the IPA and/or IPE additives were incorporated for their dewatering properties, they did not include a proportion of water.

b. Early IPA Manufacturing Processes

IPA was first produced on a large scale in the United States commencing about 1920. The process involved hydration of propene with mineral acid. In the first stage, sulfuric acid half esters were produced. During the second stage, hydrolysis took place on a continuous basis. Co-product aqueous sulfuric acid was reconcentrated by submerged combustion. High boiling organic compounds present in the diluted acid were oxidized by addition of nitric acid. Small amounts of sulfuric acid were also purged.

This two-step process had several disadvantages. The more important ones were: the conditions of the reaction were corrosive by virtue of the fact that 85% sulfuric acid was necessary for the propene esterification reaction; it was necessary to dilute the acid reaction medium to promote hydrolysis and to facilitate separation of the acid from the product alcohol after the hydrolysis reaction; acid reconcentration was required before recycle to the esterification step of the process; and there was a frequent need to neutralize the product alcohol. The cost of acid reconcentration was a major factor in the economics of the process.

c. Direct Hydration of Olefins Over a Solid Catalyst

At least as early as the 1960's, direct hydration of olefins in the vapor phase over stable catalysts was proposed as a replacement for the long practiced, two-step, sulfuric acid hydration process. Catalysts that were suggested included silicophosphoric acid, phosphoric acid on Celite, and tungstic acid on aluminum. The Veba Chemie process using a fixed bed catalyst of supported phosphoric acid gained considerable commercial usage. These vapor phase, direct hydration processes overcame certain of the major difficulties of the previously practiced two-step acid esterification-hydrolysis process. However, these processes suffered from the disadvantage of low per-pass conversion to alcohol as a result of thermodynamic, vapor phase equilibrium conditions. The low perpass conversion necessitated relatively high recycle rates to obtain the same over-all conversion obtained from the older two-step sulfuric acid dehydration process.

During the 60's, studies were also conducted to determine the usefulness of sulfonated polystyrene-divinylbenzene resins as catalysts for the selective hydration of branched olefins to form alcohols. Among the strongly acidic, ion-exchange resins of the sulfonic acid type tested, were Amberlyst 15 and IR-120, at that time available from Rohm and Haas Co. It was determined that these resins did have the ability to catalyze the hydration of olefins to alcohols, but they first had to be treated with a strong acid before use and then washed with deionized water until residual acid could no longer be found.

d. Deutsche-Texaco A.G. Process

In the early 1970's, Deutsche-Texaco A.G. (DT) reported that it had built an IPA plant using ion exchange resins based on styrene, cross-linked with varying amounts of divinylbenzene. In the DT process, a mixture of liquid water and gaseous propene was fed to the top of a reactor having four separate catalyst beds.

The water and gaseous reactant phases passed through the reactors in the same direction.

Quench water was introduced into each of the reactor beds for temperature control. Reaction temperatures of from about 270° F. to about 302° F. and pressures of from about 900 psia to about 1500 psia were maintained in the reactor beds. As the catalyst aged, the temperature of each bed was allowed to increase. Optimal molar ratios of water to propene were found to be from 12.5–15.0:1. It has been reported that polymers of propene formed when the amount of water used in the reaction mixture was below the optimal values. A conversion of up to 75% of the propene feed per-pass was said to have been realized.

The crude alcohol bottoms from the reactor unit were neutralized by addition of sodium hydroxide. IPE was stripped from the IPA-water mixture in a first distillation section. The pre-purification column bottoms from the first still were fed to another column where an azeotropic alcohol mixture was taken overhead. Final drying of the azeotrope alcohol was carried out utilizing benzene.

e. Tokyuama Soda IPA Process

In the latter part of the 1970's, Tokyuama Soda (TS) announced an IPA process carried out as a liquid-phase hydration of an olefin in the presence of a dissolved tungsten catalyst. Pulverized zirconium tungstate in an aqueous solution (polytungsten anion) was reported to be the most stable catalytic agent.

In the TS process, propene, water and recycled catalyst were preheated and pressurized before being introduced into the bottom of a reaction chamber. Reactor effluent from the upper end thereof was subjected to pressure reduction and separation of dissolved propene along with heat recovery. Unconverted propene separated by flash liberation was condensed for recycle to the reactor after purification.

An aqueous solution removed from the separator was sent to a purification section where the catalyst was removed and an azeotropic distillate containing 88% wt IPA with the remainder as water. The bottom-out water containing catalyst was recycled to the reaction section. A light-end column was provided to strip off low boiling constituents such as IPE and acetone, and the IPA was dried by benzene azeotropic distillation.

SUMMARY OF THE INVENTION a. Process

The present method is useful for preparing a motor fuel oxygenate additive which contains IPA, some IPE, and some water. A feed stock principally containing propene, along with a feed stream of water are directed to a catalytic reactor zone made up of a plurality of serially interconnected, catalytic stages each provided with a quantity of a suitable catalyst such as a particulate, cross-linked aryl sulfonic acid cation exchange resin. The propene feed stock and water are directed to the bottom inlet of the initial catalytic stage, and to the lower part of each of a plurality of catalytic stages associated therewith for exothermic reaction of the propene feed stock with the water.

The molar ratio of the water to the propene feed stock delivered to each catalytic stage is maintained within the range of from about 2:1 to about 6:1. The feed stock and water after introduction into a respective catalytic stage and the resultant IPA and IPE formed therefrom, flow in serial order through corresponding catalytic stages before exiting through the outlet of the final stage.

Reactant water which also functions as a temperature control medium is directed into each of the catalytic stages in order to maintain the temperature of the reactants in each stage within a range of from about 250° F. to about 300° F. The process is carried out under conditions such that the pressure in each of the catalytic stages is regulated at a level of from about 1200 psia to about 3000 psia. Conversions of the overall propene entering the catalytic zone up to about 92% are practical.

An important object of the invention is to simplify the process of preparing an oxygenate principally made up of IPA, along with some IPE and some water, to an extent that when the capital expense of the plant equipment, and the cost of raw materials and utilities is factored into the equation, the alcohol, ether and water blend thus produced for introduction into motor fuels is a commercially viable product not only from a functional standpoint, but from a cost point of view as well. Simplification of the process is based on the fact that only three basic units are required to produce a satisfactory motor fuel oxygenate. These three basic units include a hydrocarbon purification section, a reactor section, and a section for removal of water, purification of the unreacted hydrocarbons, and return of recycle water and unreacted hydrocarbons back to the reactor section. Several of the usual product distillation equipment and concomitant costs associated with operation thereof have been totally eliminated. In addition, significant savings are achieved by limitation of the amount of catalyst makeup required.

In the production of gasoline, about ⅓ of the feed stream derived from the crude infeed goes to the catalytic cracker. Greater than ⅔ of the infeed is converted in the FCC unit to components useful in manufacture of gasoline. For every one hundred barrels of feed to the cracker, about 7.3 barrels of propene are produced. It is conventional to direct propene and butene produced in the cracker to an alkylation unit which converts the $C_3$ and $C_4$ olefins to $C_3$ alkylates. For example, 1.0 barrel of propene plus 1.276 barrels of isobutane will produce 1.738 barrels of $C_3$ alkylate. As a consequence, only 0.76 barrel of alkylate are prepared from each barrel of propene. It is the alkylate that is a part of the final gasoline blend.

In the present process, each barrel of propene can be converted into 0.93 barrel of IPA plus IPE which can be directly incorporated into the motor fuel. The difference, (0.93 bbl.−0.764 bbl.=0.166 bbl.) is excess gasoline blending agent which is obtained from the water reacted with the propene. In view of the cost difference between water and hydrocarbons, the conversion of water to an alcohol that may be incorporated in a hydrocarbon fuel, offers significant profit potential for a refinery over existing methods. This is evident from the fact that water in purified form can be produced or purchased at a cost of roughly one cent per gallon whereas the present wholesale value of gasoline is at least about 60 cents per gallon.

b. IPA/IPE Motor Fuel Additive

The blending Reid vapor pressure (RVP) for IPE ranges from 4 to 5 psia as compared to a range of 8 to 9 psia for MTBE and 9 to 10 psia for IPA. Octane numbers measured for IPE range from about 97 to 104 for the motor method (similar to MTBE) and 107 to 113 when measured by the research method. An octane number of about 95 has been reported for IPA, 97 for ethanol, and 94 for tertiary butyl alcohol (TBA). In like manner, a research octane number of 117 has been reported for IPA, 121 for ethanol, 106 for TBA, 115 for MTBE and 108 for TAME.

The mass exhaust emissions from IPE gasoline blends using identical refinery gasoline components for a given oxygen content are reported to have been found similar to those of MTBE and TAME blends. It is of note in this respect that prior investigators have found that propionaldehyde does not appear in the exhaust of gasoline motor fuels containing IPE. This is to be contrasted with the fact that formaldehyde appears in the exhaust of gasoline motor fuels containing methanol and acetaldehyde at a significantly lower concentration than such constituents have been found in the exhaust of gasoline motor fuels containing ethanol.

IPE has been found to be as compatible as MTBE in tests for demulsifier compatibility, multi-metal corrosion protection, fuel filterability and anti-oxidant performance when compared at 2.0 weight percent and 2.7 weight percent oxygen content with a commercially available additive package. Overall driveability indexes were found to be similar using IPA and MTBE gasoline motor fuels having the same hydrocarbon base. Trained rater driveability test showed IPE to provide similar or better performance than other ethers, including MTBE at a 3.5 weight percent fuel oxygen level. IPE has been found to be consistently similar to MTBE in terms of distillation effects, cold starts, and warm up driveability. Fleet tests with IPE blends generated positive consumer response and have not produced any vehicle durability problems.

Toxicology tests to date indicate that IPE is not mutagenic, cytotoxic, or clastogenic and are unlikely to be carcinogenic.

Although IPA has not has yet been thoroughly investigated as a motor fuel additive, it was investigated and found to be an excellent aviation gasoline components during the Second World War. IPA performance is at least equivalent to or better than ethanol for the same oxygen content. Unlike ethanol, IPA has no water compatibility problems and in fact is an excellent co-solvent. In this manner, the problems encountered by addition of methanol or ethanol to motor fuels can be alleviated. Similarly, IPA can be used for higher oxygen content concentrations without the danger of not being sufficiently soluble when blended with any of the conventional refinery hydrocarbon fuel components.

DESCRIPTION OF THE PREFERRED EMBODIMENT

Figure 1A:
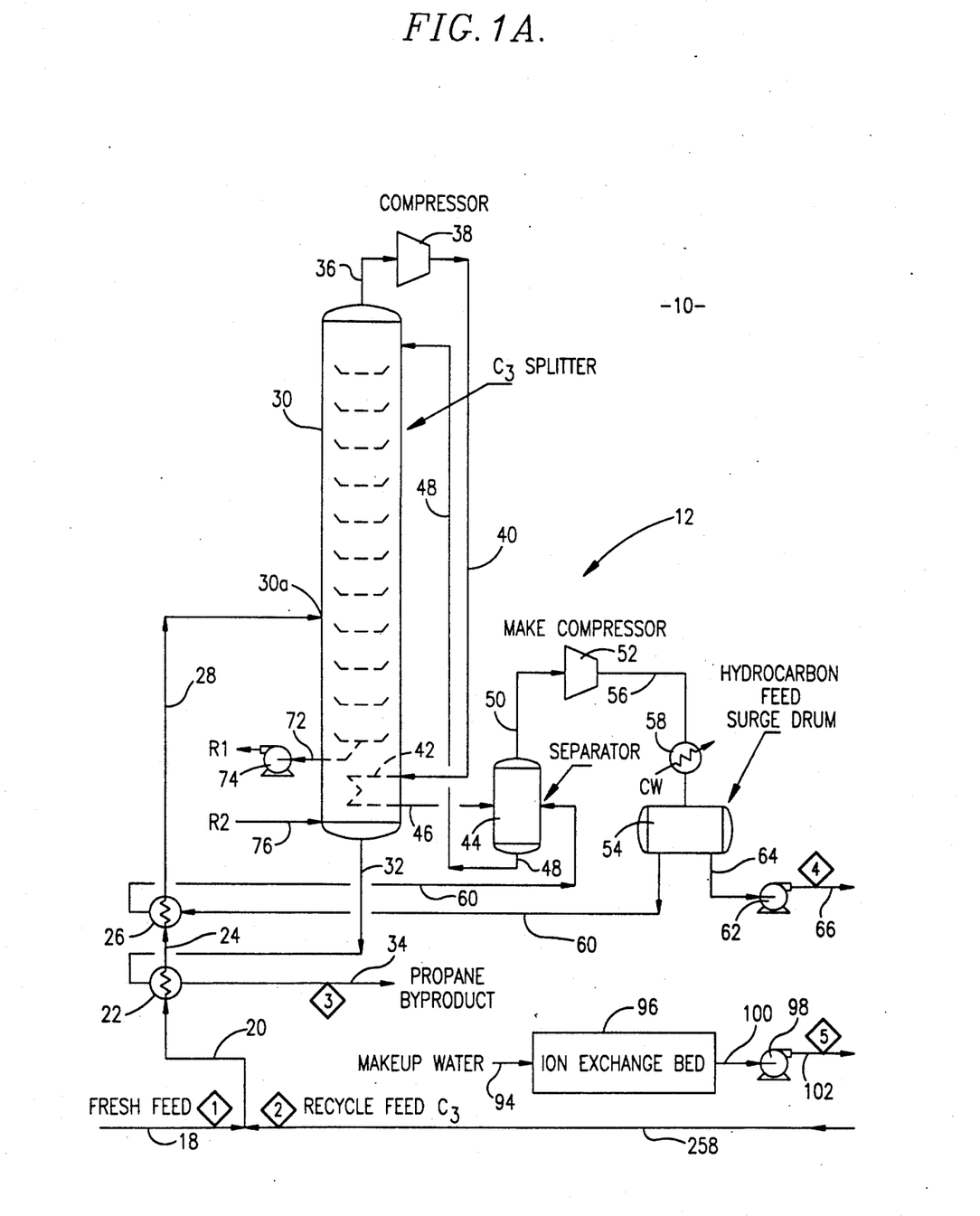
FIGS. 1A, 1B and 1C are schematic diagrams of apparatus for preparing an oxygenate from a $C_3$ olefin feed stream wherein the oxygenate contains isopropanol, diisopropyl ether and some water, that may be used as a motor fuel additive.
Figure 1B:
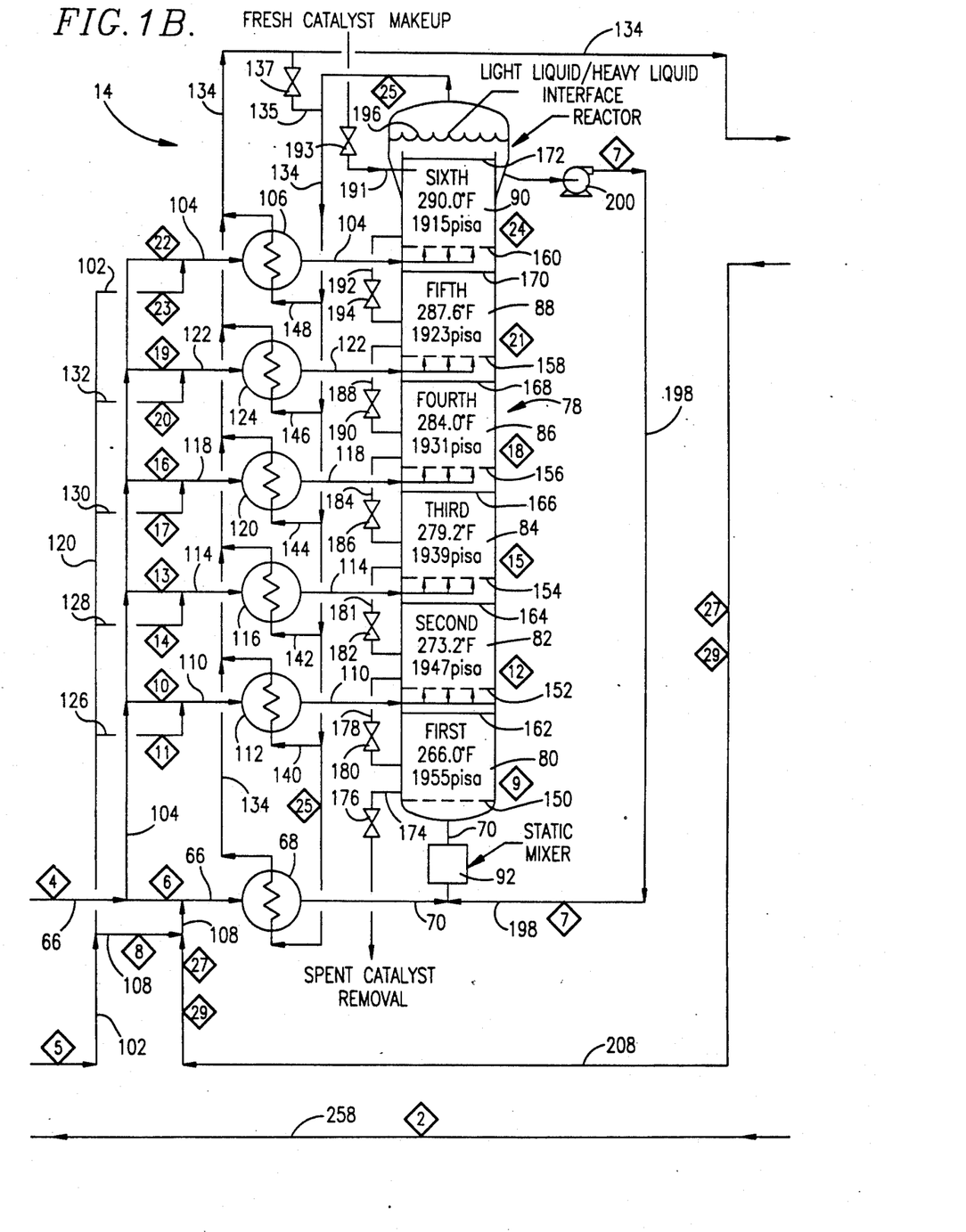
Figure 1C:
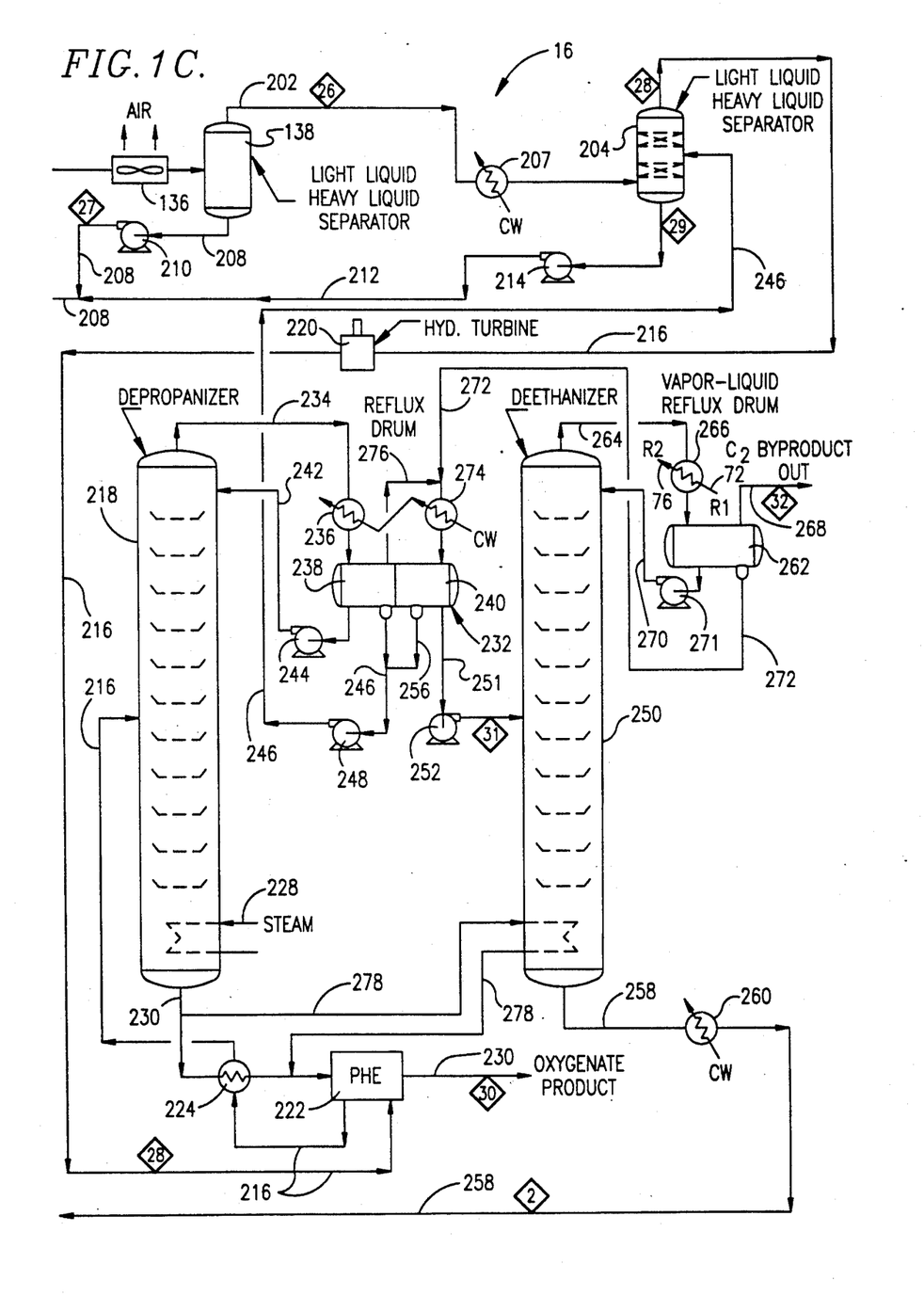

Apparatus broadly designated 10 in FIGS. 1A, 1B and 1C permits economical production of an oxygenate for addition to motor fuels, and is made up of only three basic units. Those units include hydrocarbon splitting section 12 (FIG. 1A), reactor section 14 (FIG. 1B), and oxygenate separation section 16 (FIG. 1C) for separating the oxygenate product from unreacted hydrocarbons and water.

Referring initially to FIG. 1A, fresh hydrocarbon feed is introduced into apparatus 10 through line 18. The feed typically is made up principally of propene, varying quantities of propane, and incidental amounts of hydrocarbons including ethylene, ethane and isobutane. Fresh feed line 18 is connected to a line 20 which is joined to the infeed of one side of a heat exchanger 22. The second side of heat exchanger 22 is connected by line 24 to the inlet of one side of a second heat exchanger 26. The other side of that heat exchanger is joined by line 28 to a propene splitter tower 30. Line 28 is preferably connected to tower 30 intermediate the upper and lower ends thereof at a point 30a as indicated schematically in FIG. 1A. The propane bottoms from tower 30 are removed therefrom via line 32 which is connected to heat exchanger 22 to bring the bottoms into heat exchange relationship with the fresh propene feed with tower 30. Propane by-product is directed to a point of use by a line 34 which is connected to an outlet of the heat exchanger 22.

The propene feed overhead from tower 30 exits therefrom via line 36 which is joined to the suction side of a compressor 38. The pressure side of compressor 38 is connected by line 40 to a heat exchange section 42 within tower 30 adjacent the lower portion thereof. The outlet of heat exchange section 42 is connected to a separator 44 by a line 46. The liquid bottoms from separator 44 are returned to the upper part of tower 30 by a line 48 joined to the lower end of separator vessel 44. The propene overhead from separator 44 leaves that vessel via line 50 which is connected to the suction side of make compressor 52.

The pressurized gaseous output from compressor 52 is directed into hydrocarbon feed surge drum 54 by a line 56 which passes through a cooling water heat exchanger 58. A liquid return line 60 extends through heat exchanger 26 and is joined to separator 44. The propene feed from surge drum 54 is connected to pump 62 by a line 64 while the output from the pump 62 is directed via line 66 to a first input side of a heat exchanger 68 (FIG. 1B). The output of the first side of heat exchanger 68 has a line 70 joined thereto.

Liquid product within splitter tower 30 is removed from the lower end of the tower by a line 72 having a pump 74 interposed therein. A line 76 for return of liquid to tower 30 is connected to the lowermost part of tower 30. Lines 72 and 76, designated as R1 and R2 respectively in FIG. 1A, are joined to lines R1 and R2 of heat exchanger 266 of FIG. 1C which will be described in detail hereafter.

The primary component of reactor section 1B is an upright catalytic reactor vessel broadly designated 78 which in a preferred embodiment has six catalytic reaction stages designated as, first reaction stage 80, second reaction stage 82, third reaction stage 84, fourth reaction stage 86, fifth reaction stage 88 and sixth reaction stage 90.

The propene feed line 70 from heat exchanger 68 is connected to the lower end of vessel 78 for introduction into the catalytic reaction stage 80. A static mixer 92 is interposed in line 70 ahead of the vessel inlet. Referring to FIG. 1A, makeup water for the hydration process is supplied through line 94 leading to an ion exchange bed 96 serving to remove impurities and minerals from the water. The outflow from bed 96 is connected to a pump 98 by a line 100. The output line 102 of pump 98 is connected to a main manifold propene feed line 104 which extends through heat exchanger 106 shown schematically adjacent at the upper part of reactor vessel 78, and is connected to the lower end of sixth catalytic stage 90 of reactor vessel 78. A line 108 connected to makeup water line 102 is joined to propene feed line 66 by a line 108.

A secondary manifold feed line 110 extends through the heat exchanger 112 and is joined to the lower part of second catalytic stage 82. In like manner, a secondary manifold feed line 114 extends through heat exchanger 116 and is connected to the lower part of third catalytic stage 84. Secondary manifold feed line 118 extends through heat exchanger 120 and is coupled to the lower part of fourth catalytic reactor stage 86. Finally, a secondary manifold feed line 122 extend through heat exchanger 124 and leads to the lower end of fifth catalytic reactor stage 86. Water supply lines 126 between line 102 and line 110, line 128 between line 102 and line 114, line 130 between line 102 and line 118 and line 132 between line 102 and line 122, allow water to be introduced into the propene feed directed into the second through fifth catalytic stages of reactor vessel 78.

The overhead from reactor vessel 78 is removed therefrom via a line 134 connected at the top of vessel 78 and extending through heat exchanger 68 in heat exchange relationship with the propene feed. A by-pass line 135 having a control valve 137 therein joins two adjacent sections of line 134 on the opposite sides of the serially arranged heat exchanger 68, 112, 116, 120, 124, and 106. Line 134 also passes through an air cooled heat exchanger 136 and is connected to the light heavy liquid separator 138 (FIG. 1C). It is to be observed from FIG. 1C that heat exchanger 136 brings cooling air into heat exchange relationship with the stream flowing therethrough.

Line 140 extending through heat exchanger 112, line 142 extending through heat exchanger 116, line 144 extending through heat exchanger 120, line 146 extending through heat exchanger 124 and line 148 extending through heat exchanger 106 permit the output stream flowing through line 134 from the upper end of vessel 78 to be brought into heat exchange relationship with propene and water feed lines 110, 114, 118, 124 and 104 respectively, with the return of such lines being to line 134 after the stream flowing therethrough has passed through heat exchanger 68.

Each of the catalytic stages 80–90 respectively function as fluidized beds. The catalyst in each stage may be of a particulate sulfonated polystyrene-divinyl benzene resin such as Rohm & Haas IR-120 or Dow Chemical Dowex 50 being specific examples in this respect. Distributors 150, 152, 154, 156, 158 and 160 within reactor vessel 78 serve to support the particulate catalyst within each of the stages 80–90 inclusive. Suitable stage distributors in this respect include a Johnson-type screen or a perforated plate with openings small enough to retain the catalyst particles when flow is interrupted. A plate with 7/64 in. diameter perforations is satisfactory in this respect. The top of the fluidized catalytic bed of first reactor stage 80 is schematically depicted by the numeral 162. The upper level of the fluidized catalytic beds of the second through sixth catalytic reactor stages 82–90 within vessel 78 are likewise indicated schematically in FIG. 1B by lines 164 through 172 respectively. It is to be understood though, that the column defined by catalytic stages 80–90 is completely filled with liquid plus catalytic particles.

Upwardly directed arrows at the lower extremities of the second through sixth reactor stages 82–90 schematically represent delivery of propene feed and water to the lower part of these stages for upward flow through a screen immediately thereabove. It is likewise to be understood that propene feed and water introduced into the lower part of stage 80 via line 70 flows upwardly through the screen 150.

A portion of the solid catalyst within first catalytic stage 80 may be removed therefrom via a catalyst transfer line 174 having a normally closed, selectively openable valve 176 therein. In a similar manner, a portion of the catalyst from the second catalytic stage 82 may be removed therefrom and redirected into the first catalytic stage 80 through a transfer line 178 having a selectively manipulable valve 180. Transfer line 181 having a selectively openable valve 182 therein between catalytic stages 84 and 82, transfer line 184 having a valve 186 therein, transfer line 188 having a valve 190 therein, and transfer line 192 having a valve 194 therein permit catalyst to be removed from the second catalytic stage 82 and returned to the first catalytic stage 80, removed from the third catalytic stage 84 and redirected into the second catalytic stage 82, removed from the fourth catalytic stage 86 and returned to the third catalytic stage 84, removed from the fifth catalytic stage 88 and returned to the fourth catalytic stage 86, and removed from the sixth catalytic stage 90 and returned to the fifth catalytic stage 88 respectively. Line 191 extending through the top of reactor 78 and which is provided with a selectively openable valve 193, projects into stage 90 and permits fresh makeup catalyst to be introduced into the sixth stage 90.

The heavy liquid/light liquid interface at the top of vessel 78 is indicated schematically by the scalloped line 196. Aqueous heavy liquid is removed from below level 196 at the upper end of vessel 78 by a line 198 having a pump 200 therein, and which connects to line 70 upstream of static mixer 92.

Viewing FIG. 1C, the stream introduced into separator vessel 138 is separated into fractions with the overhead therefrom passing through line 202 to the light-heavy liquid separator 204. Before entering vessel 204, the stream flowing through line 202 passes in heat exchange relationship with cooling water supplied to heat exchanger 207.

The underflow from separator vessel 138 is directed to line 108 via line 208 having a pump 210 therein. The bottoms from separator vessel 204 are directed to line 208 by a line 212 having a pump 214 interposed therein.

The overhead from separator vessel 204 is directed via line 216 to depropanizer distillation vessel 218 intermediate the upper and lower ends thereof. It can be seen from FIG. 1C that the stream flowing in line 216 first passes through turbine 220, next through one side of a plate heat exchanger 222, and then through one side of a tube and shell heat exchanger 224. Steam is introduced into the lower end of still 218 by steam supply and return line 228.

The bottoms from still 218, constituting oxygenate product, are removed the vessel via line 230 which extends through heat exchanger 224 in heat exchange relationship with the flow through 216, and through the heat exchanger 222.

The overhead from depropanizer 218 is directed via line 234 to a reflux drum broadly designated 232. The stream flowing through line 234 is first brought into heat exchange relationship with cooling water flowing through heat exchanger 236. As is evident from FIG. 1C, reflux drum 232 has two sections, 238 and 240 respectively. The line 234 is connected to section 238 of drum 232, with a part of the outflow from section 238 being returned to the upper end of depropanizer 218 by line 242 provided with a pump 244 therein. The underflow from section 238 of drum 240 is removed therefrom via line 246 having a pump 248 therein which returns the collected liquid to separator 204 intermediate internal separators within the vessel. Line 246 connects to separator drum 204 intermediate the ends thereof between upper and lower separator sections shown by dotted lines in FIG. 1C. A portion of the outflow from section 240 of drum 232 is introduced into a central part of deethanizer distillation vessel 250 by a line 251 having a pump 252 therein. The underflow from section 240 of drum 232 is directed into line 246 by line 256.

The bottom outflow from deethanizer 250 is returned to feed line 20 by a line 258 which first passes in heat exchange relationship with cooling water directed through heat exchanger 260. The overhead from deethanizer 250 is directed to vapor-liquid reflux drum 262 through a line 264 connected to the top of vessel 250. The stream flowing through line 264 first passes through a heat exchanger 266 which brings the product stream into heat exchange relationship with cooling water. Ethane and ethylene by-products are removed from drum 262 via line 268. A portion of the outflow from reflux drum 262 is returned to the upper end of deethanizer 250 by a line 270 having a pump 27i therein while the bottoms from drum 262 are directed into section 240 of reflux drum 232 through a line 272. The stream flowing through line 272 first passes through heat exchanger 274 before flowing into section 240. Heat exchanger 236 and 274 receive cooling water which is in series relationship as indicated by the schematic representation of FIG. 1C. The overhead from reflux drum 238 is introduced into line 272 through a line 276 which is connected to line 272 upstream of heat exchanger 274.

By-pass line 278 connected to line 230 ahead of heat exchanger 234 serves to divert a portion of the bottoms from depropanizer 218 through deethanizer 250 and to then return such stream to line 230 intermediate heat exchangers 222 and 224.

It is to be observed from the right-hand portion of FIG. 1C that the heat exchange medium passed through heat exchanger 266 upstream of vapor-liquid reflux drum 262 is derived lines 72 and 76 joined to splitter 30.

OPERATION OF THE PREFERRED EMBODIMENT

For a better understanding of the operation of apparatus 10, the box score of Table I hereunder sets forth a representative material balance for a typical process that may be advantageously carried out in accordance with the present invention to prepare an oxygenate additive for blending with motor fuel. It is to be understood in this respect that the specific parameters set out in the box score are for exemplary purposes only and are not intended as a limitation on the process. The material balance illustrates typical conditions that may be employed to produce oxygenate by hydration of an olefin wherein a feed stream such as propene is reacted with water to produce either IPA or IPE.

TABLE I

| Stream No. | S-1 Fresh Feed | S-2 Recycle | S-3 Propane Product | S-4 HC Feed to Reactor | S-5 Makeup Water | S-6 HC Feed To 1st Stage | S-7 Recycle to 1st Stage | S-8 Water to 1st Stage | S-9 1st Stage Effluent | S-10 HC Feed to 2nd Stage | S-11 Water to 2nd Stage | S-12 2nd Stage Effluent | S-13 HC to 3rd Stage | S-14 Water to 3rd Stage | S-15 3rd Stage Effluent | S-16 HC to 4th Stage | S-17 Water to 4th Stage |
|---|---|---|---|---|---|---|---|---|---|---|---|---|---|---|---|---|---|
| Temp. (F.) | 90 | 90 | 85 | 113 | 113 | 113 | 290 | 113 | 266 | 113 | 113 | 273.2 | 113 | 113 | 279.2 | 113 | 113 |
| Pressure (psia) | 200 | 200 | 150 | 2000 | 2000 | 2000 | 1915 | 2000 | 1955 | 2000 | 2000 | 1947 | 2000 | 2000 | 1939 | 2000 | 2000 |
| Ethylene (Mol/Hr) | 0.3120 |  |  | 0.3120 |  | 0.0773 |  |  | 0.0773 | 0.0488 |  | 0.1255 | 0.0481 |  | 0.1733 | 0.0472 |  |
| Ethane (Mol/Hr) | 1.5580 | 0.0020 | 0.0020 | 1.5580 |  | 0.3861 |  |  | 0.3861 | 0.2436 |  | 0.6296 | 0.2402 |  | 0.8698 | 0.2358 |  |
| Propene (Mol/Hr) | 432.9750 | 42.7500 | 0.6992 | 475.0258 |  | 117.7125 | 0.0010 |  | 42.7522 | 74.2776 |  | 42.7521 | 73.2661 |  | 42.7521 | 71.8915 |  |
| Propane (Mol/Hr) | 101.2600 | 10.0027 | 101.2827 | 9.9400 |  | 2.4632 | 0.0002 |  | 2.4656 | 1.5542 |  | 4.0250 | 1.5331 |  | 5.5669 | 1.5043 |  |
| C4's (Mol/Hr) | 0.9990 |  | 0.9990 |  |  |  |  |  |  |  |  |  |  |  |  |  |  |
| Water (Mol/Hr) |  |  |  |  | 431.2329 |  | 197.4089 | 68.0155 | 302.0084 |  | 82.9079 | 309.8918 |  | 78.2037 | 317.0008 |  | 73.2951 |
| Acetone (Mol/Hr) |  |  |  |  |  |  |  |  | 0.0024 |  |  | 0.0076 |  |  | 0.0164 |  |  |
| Ethanol (Mol/Hr) |  |  |  |  |  |  | .0001 |  | 0.0004 |  |  | 0.0007 |  |  | .0010 |  |  |
| IPE (Mol/Hr) |  |  |  |  |  |  |  |  | 0.1854 |  |  | 1.5146 |  |  | 3.5828 |  |  |
| IPA (Mol/Hr) |  |  |  |  |  |  | 0.2804 |  | 74.7915 |  |  | 146.4869 |  |  | 215.3406 |  |  |
| n-PA (Mol/Hr) |  |  |  |  |  |  | 0.0009 |  | 0.0830 |  |  | 0.1620 |  |  | 0.2378 |  |  |
| C6 = (Mol/Hr) |  |  |  |  |  |  |  |  | 0.0003 |  |  | 0.0021 |  |  | 0.0054 |  |  |
| C6OH (Mol/Hr) |  |  |  |  |  |  |  |  |  |  |  | 0.0011 |  |  | 0.0031 |  |  |
| C9 = (Mol/Hr) |  |  |  |  |  |  |  |  |  |  |  | 0.0002 |  |  | 0.0005 |  |  |
| C9OH (Mol/Hr) |  |  |  |  |  |  |  |  |  |  |  |  |  |  | 0.0001 |  |  |
| TOTAL | 537.1040 | 52.7547 | 102.9829 | 486.8358 | 431.2329 | 120.6391 | 197.6915 | 68.0155 | 422.8356 | 76.1242 | 82.9079 | 505.5992 | 75.0875 | 78.2037 | 585.4958 | 73.6788 | 73.2951 |

| Stream No. | S-18 Effluent from 4th Stage | S-19 HC to 5th Stage | S-20 Water to 5th Stage | S-21 5th Stage Effluent | S-22 HC to 6th Stage | S-23 Water to 6th Stage | S-24 Effluent From 6th Stage | S-25 Light Liquid | S-26 Air Cooled Light Liquid | S-27 130° F. Aqueous Phase | S-28 Deprop. Feed | S-29 92° F. | S-30 Oxygenate Product | S-31 Deethanizer Feed | S-32 Overhead Product |
|---|---|---|---|---|---|---|---|---|---|---|---|---|---|---|---|
| Temp. (F.) | 284 | 113 | 113 | 287.6 | 113 | 113 | 290 | 290 | 130 | 130 | 92 | 92 | 324 | 86 | 38 |
| Pressure (psia) | 1931 | 2000 | 2000 | 1923 | 2000 | 2000 | 1915 | 1915 | 1885 | 1885 | 1870 | 1870 | 200 | 190 | 400 |
| Ethylene (Mol/Hr) | 0.2202 | 0.0460 |  | 0.2659 | 0.0446 |  | 0.3102 | 0.3102 | 0.3102 |  | 0.3102 |  |  | .3102 | 0.3102 |
| Ethane (Mol/Hr) | 1.1056 | 0.2299 |  | 1.3355 | 0.2225 |  | 1.5600 | 1.5600 | 1.5600 |  | 1.5600 |  |  | 1.5600 | 1.5580 |
| Propene (Mol/Hr) | 42.7521 | 70.0716 |  | 42.7521 | 67.8065 |  | 42.7521 | 42.7511 | 42.7510 | 0.0001 | 47.7510 |  | 0.0006 | 42.7504 | 0.0004 |
| Propane (Mol/Hr) | 7.0840 | 1.4663 |  | 8.5671 | 1.4189 |  | 10.0070 | 10.0070 | 10.0070 |  | 10.0070 |  | 0.0043 | 10.0027 |  |
| C4's (Mol/Hr) |  |  |  |  |  |  |  |  |  |  |  |  |  |  |  |
| Water (Mol/Hr) | 322.4301 |  | 67.7224 | 326.2634 |  | 62.0884 | 328.6514 | 132.2424 | 34.6475 | 97.5949 | 23.5876 | 13.6597 | 20.9872 | 0.0035 | 0.0006 |
| Acetone (Mol/Hr) | 0.0292 |  |  | 0.0460 |  |  | 0.0670 | 0.0670 | 0.0670 |  | 0.0670 |  | 0.0670 |  |  |
| Ethanol (Mol/Hr) | .0013 |  |  | .0016 |  |  | 0.0019 | 0.0018 | .0018 |  | 0.0018 |  | .0018 |  |  |
| IPE (Mol/Hr) | 7.5798 |  |  | 13.7232 |  |  | 21.7786 | 21.7786 | 21.7786 |  | 27.7786 |  | 21.7786 |  |  |
| IPA (Mol/Hr) | 279.1219 |  |  | 336.7805 |  |  | 388.3384 | 388.0579 | 388.0486 | 0.0093 | 388.0481 | 0.0005 | 388.0481 |  |  |
| n-PA (Mol/Hr) | 0.3080 |  |  | 0.3715 |  |  | 0.4283 | 0.4274 | 0.4273 | 0.0001 | 0.4273 |  | 0.4273 |  |  |
| C6 = (Mol/Hr) | 0.0107 |  |  | 0.0181 |  |  | 0.0277 | 0.0277 | 0.0277 |  | 0.0277 |  | 0.0277 |  |  |
| C6OH (Mol/Hr) | 0.0071 |  |  | 0.0133 |  |  | 0.0219 | 0.0219 | 0.0219 |  | 0.0219 |  | 0.0219 |  |  |
| C9 = (Mol/Hr) | 0.0009 |  |  | 0.0014 |  |  | 0.0020 | 0.0020 | 0.0020 |  | 0.0020 |  | 0.0020 |  |  |
| C9OH (Mol/Hr) | 0.0003 |  |  | 0.0006 |  |  | 0.0010 | 0.0010 | 0.0010 |  | 0.0010 |  | 0.0010 |  |  |
| TOTAL | 660.6512 | 71.8138 | 67.7224 | 730.1402 | 69.4925 | 62.0084 | 795.1653 | 597.2560 | 510.6516 | 97.5954 | 449.5912 | 13.6602 | 430.1127 | 54.6268 | 1.8692 |

For convenience, the principle streams of the illustrative process as set out in the schematic representations of FIGS. 1A 1B and 1C are keyed to the box score of Table I by numbers within a diamond. In the description hereof, the streams coded by a diamond in the drawing are identified as "S-n" wherein "S" represents "Stream" and "n" is the number assigned to that stream in the box score.

From the box score of Table I it can be seen that in the representative process, the fresh feed introduced into apparatus 10 via line 18 and identified as stream S-1 and which may for example be supplied from a petroleum refinery process, typically is made up of a majority of propene, a lesser proportion of propane, and minor amounts of ethylene, ethane and $C_4$ hydrocarbons. That stream, which for instance, may be supplied at a temperature of 90° F. and a pressure of 200 psia is heat exchanged with the propane bottoms from splitter 30, as well as a part of the outflow from hydrocarbon surge feed drum 54 in heat exchanger 26 before being introduced into a central part of vessel 30 via lines 20, 24 and 28. The propane by-product bottoms from the splitter 30 removed therefrom via line 32, in the exemplary material balance, is principally propane. It also contains any $C_4$ hydrocarbons introduced into the fresh feed together with limited amounts of propene.

The gaseous overhead from splitter 30, which is primarily propene is removed from the column through line 36, and after being compressed in compressor 38, and following passage thereof through the heat exchange section 42 within the lower part of vessel 30, flows into separator 44. Thus, flexibility is achieved in the heat balance for the $C_3$ splitter 30, particularly in light of the fact that the heat of compression by compressor 38 serves to increase the stripping capacity of the tower 30. Liquids produced as a result of heat exchange of the propene feed stream in the lower part of vessel 30 are collected in separator 44 and returned via line 48 to the top of tower 30. The gaseous propene overhead from separator 44 after being further compressed by make compressor 52 is heat exchanged with cooling water in heat exchanger 58 and then introduced into the hydrocarbon surge feed drum 54. As previously indicated, a part of the outflow from surge drum 54 is returned to separator 44 via line 60 which brings the stream into heat exchange relationship with the feed gas stream through the medium of heat exchanger 26.

The feed stream outflow S-4 from hydrocarbon feed surge drum 54 leaves that vessel through line 64, and is pumped by pumps 62 to a pressure of about 2000 psia. The propene content of feed stream S-4 is of the order of about 98%.

Makeup water supplied through line 94 is passed through an ion exchange bed 96 to remove cations and-/or mineral impurities in the water. If cations were permitted to remain in the makeup water they would neutralize the sulfonic acid sites of the sulfonic acid resin catalyst thereby causing deactivation of the catalytic agent, and decrease the desired hydration reactions, i.e., formation of IPA or IPE from the propene and water entering reactor 78. The infeed to the first catalytic stage 80 is made up of propene, recycle water and fresh makeup water. The composition of such infeed is therefore the combination of stream S-8 (makeup water), stream S-6 (propene), and stream S-7 (recycle water).

Simultaneously with introduction of propene and water reactants into the first catalytic stage 80, propene and water are also directed into the reactor vessel 78 at the second, third, fourth, fifth and sixth stages 82-90 respectively. As is most apparent from FIG. 1B, propene stream S-10 is introduced into the second catalytic stage 82 in conjunction with makeup water stream S-11. In like manner, propene stream S-13 along with makeup water stream S-14 is directed into the third catalytic reaction stage 84. Propene stream S-16 along with makeup water stream S-17 is introduced into the fourth catalytic stage 86, propene stream S-19 along with makeup water stream S-20 is directed to the fifth catalytic reaction stage 88 and propene feed stream S-22 in conjunction with makeup water stream S-23 is directed to the sixth catalytic reaction stage 90.

The flow rates of the various propene feed streams, as well as the flow rates of makeup water and recycle water as appropriate, and the temperature conditions thereof, are correlated with the catalytic reactions taking place in the first through sixth catalytic stages 80-90 to maintain the specified temperature and pressure parameters within each stage substantially at the average values indicated in FIG. 1B. Control of the temperature in each of the reactor stages at substantially the value indicated for each stage has the concomitant effect of maintaining the pressure in each reactor stage at the levels set out in FIG. 1B. Thus, the reactants in first stage 80 are maintained at a temperature of about 266° F. with a resulting pressure of about 1955 psia, the temperature of the reactants in the second catalytic stage 82 is maintained at the indicated temperature of about 273.2° F. and thus producing a pressure of about 1947 psia, the temperature of the reactants in the third catalytic stage 84 is maintained at about 279.2° F. thus providing a pressure of about 1939 psia, the reactants in the fourth stage 86 are maintained at about 284° F. with a pressure of about 1931 psia being maintained, the temperature of the reactants in the fifth stage 88 is maintained at a level of about 287.6° F. with a concomitant pressure of about 1923 psia, and the temperature of the reactants in the sixth catalytic stage are maintained at about 290° F. with a corresponding pressure of about 1915 psia. Hydraulic turbine 220 controls the back pressure on stages 80-90 to maintain the specified pressure conditions within each of the stages.

The amount of heat transferred from respective heat exchangers 68, 112, 116, 120, 124 and 106 to streams S-6, S-10-11, S-13-14, S-16-17, S-19-20, and S-22-23 may be adjusted by selective control of the proportion of streams S-25 that is permitted to flow in by-passing relationship to the heat exchangers via line 135.

Close control over the temperature of the catalytic beds 80-90 respectively is assured by virtue of the fact that the propene and water feed streams to each of the catalytic stages are brought into heat exchange relationship with the stream S-25 overhead flow from reactor vessel 78, through heat exchanger 68, 112, 116, 120, 124 and 106 respectively, which are connected in parallel across stream S-25. The less dense liquid overhead stream S-25 which exits from reactor vessel 78 via line 134 contains nearly all of the oxygenate product and unreacted hydrocarbons. A comparatively small amount of $C_3$ alcohols remain dissolved in the more dense liquid phase below line 196 which is drawn from the upper end of the reactor 78 through line 198.

Controlling the initial stage temperature in stage 80 to maintain a level which is significantly lower than temperature of the final stage of stage 90 offsets the initially higher concentration of propene feed to the lowermost catalytic stage of the reactor 78. Lower concentration of propene is inherent in succeeding stages by virtue of dilution effects. The surrounding fluid temperature which is cooler in the initial catalytic stage 80 also acts to offset the higher exothermic heat attributable to a greater quantity of catalytic reactions occurring in surrounding relationship to each catalytic particle in the first stage than in latter stages as a result of a more favorable equilibrium and negligible product concentrations in the incoming feed. The lower fluid temperature in the first or initial stage 80 also off-sets the fact that the concentration of propene is highest in the first stage, where the pressure is also the highest. High temperatures and pressures tend to increase the probability of localized polymer reaction, particularly if mal-distribution of the reactants occurred or there was an absence or a limitation of water flow around the individual catalyst particles.

In the present process however, absence of water around each catalyst particle, or restriction of water flow past the catalyst particles is avoided by virtue of the provision of the aqueous phase which constitutes a continuous fluid in the liquid fluidized catalytic stage. Localized hot spots are thus precluded which would otherwise be precursors of oligomers.

It is also important to note in this respect that the increase in temperature between proximal catalytic stages starting with stage 80 and progressing toward stage 90 is limited to a value within a range of from about 2° F. to about 8° F., with the range in the specific example given being about 7.2° F. difference between stages 80 and 82, and 2.4° F. difference between stages 88 and 90.

In view of the fact that the driving force for reaction of propene with water favors formation of IPA over IPE, the fact that the present process results in some IPE being produced in the first stage is evidence of the efficiency of reactor 78, and particularly of the efficient utilization of the fluidized catalytic bed making up initial stage 80.

The exothermic reaction that takes place in initial catalytic stage 80 makes it unnecessary to add heat to the reactants other than the heat supplied by the water recycle stream S-7 which is at a temperature of 290° F. and the heat made available to the propene feed which is heat exchanged in exchanger 68 with the overhead from reactor 78, also at 290° F. The propene feed to each of the stages 82-90 is also preheated to some extent by passage in heat exchange relationship with the overhead from reactor 78 through the provision of heat exchangers 112, 116, 120, 124 and 106. The first stage propene feed reactor organic phase effluent heat exchanger 68 is constructed to provide a reasonable temperature approach to the leaving reactor organic phase. First stage bed temperature control is achieved by by-passing a portion of the cold propene feed around heat exchanger 68. Only a limited amount of cold propene feed by pass is required.

The molar ratio of water to propene delivered to each of the catalytic stages 80-90 inclusive is desirably maintained within the range of from about 2:1 to about 6:1, and preferably from about 2:1 to about 4:1. The molar ratio of water to propene entering the first stage is controlled most preferably from about 2.5:1 to about 3.5:1. In an exemplary process, the water to propene molar ratios may be expressed as follows:

TABLE II

| Catalytic Stages | Water | Propene | Molar Ratio |
| --- | --- | --- | --- |
| In to Stage 80 | 3939.68 | 1231.15 | 3.200 |
| Out from Stage 80 | 3140.20 | 427.38 | 7.348 |
| In to Stage 82 | 4000.71 | 1225.96 | 3.263 |
| Out from Stage 82 | 3218.43 | 427.38 | 7.531 |
| In to Stage 84 | 4029.30 | 1184.75 | 3.401 |
| Out from Stage 84 | 3293.15 | 427.38 | 7.703 |
| In to Stage 86 | 4022.90 | 1135.22 | 3.545 |
| Out from Stage 86 | 3358.58 | 427.38 | 7.859 |
| In to Stage 88 | 4018.17 | 1093.36 | 3.675 |
| Out from Stage 88 | 3418.53 | 427.38 | 7.999 |
| In to Stage 90 | 4005.97 | 1027.18 | 3.900 |
| Out from Stage 90 | 3471.63 | 427.38 | 8.123 |

The flow rates of propene streams S-10, S-13, S-16, S-19 and S-22 are controlled so that the amount of propene injected into each of the stages 82-90 inclusive is generally equivalent to the propene which reacts in a given stage.

The molar ratio of water which reacts with propene introduced into respective catalytic stages increases as the temperature of corresponding catalytic beds increases, and as the percent of conversion rises. A favorable water to olefin ratio is therefore maintained by injecting a slight excess of water over that chemically consumed in each catalytic stage 80-90. A higher water to propene molar ratio than specified herein would result in a decrease in the amount of diisopropyl ether formed. IPE is a desirable constituent when producing an oxygenate motor fuel additive.

The aqueous liquid phase in each of the catalytic stages 80-90 functions as a continuous phase during operation of reactor 76 under preferred conditions. Nearly all of the organic products produced enter the less dense liquid phase which contains unreacted hydrocarbon feed constituents. The surrounding aqueous continuous phase has been found to contain a limited concentration of dissolved IPA with negligible IPE content, even in stage 90. Individual catalyst particles, which are maintained in a fluidized state by the upwardly moving fluid phases, cause the aqueous continuous phase velocity to become more effective as a fluidizing medium for stages 80-90 by virtue of the fact that its velocity is increased by the displaced volume occupied by the more buoyant concurrent moving lighter liquid phase droplets. Unlike the continuous aqueous liquid phase, this lighter phase is dispersed in a discontinuous form, primarily as liquid droplets for the product of this first stage 80 on toward final stage 90. Coalescing of smaller droplets into larger size droplets occurs in the downstream catalytic stages of the reactor 76. Such larger agglomerations of the lighter organic liquid phase which contains all the propene, are again initially redispersed into droplets of limited size by a succeeding stage distributor plate so that excellent mass transfer of the propene is facilitated to participate in the desired hydrolysis reactions.

As long as two liquid phases exist from an equilibrium viewpoint, the fluidized bed arrangement of the present process assures the presence of water at each catalyst particle, because each catalyst particle is bathed aqueous fluid. Presence of water is thus assured and supported by the upper flowing at each catalyst particle. Inhibition of oligomer formation results in addition to water being available for the desired hydration reactions. Diffusion of IPA and IPE formed at the surfaces of the catalyst particles is favored by the generally low oxygenate concentration in the moving surrounding aqueous liquid phase. Movement of the fluidized catalyst particles acts to enhance the mass transfer of formed oxygenate products from the catalyst particle surface to surrounding fluids to eventually become part of the dispersed lighter organic phase fluid. The more buoyant organic liquid phase droplets concurrently continue upward in the reactor stage at a slightly faster rate than the aqueous phase continuous liquid.

The two fluid phases have an active interchange because of fluidization. The dispersed organic phase, which contains nearly all of the hydrocarbon reactant, including unreacted propene, has frequent periodic direct contact with individual catalyst particles. Because of the area provided by the droplets containing the propene reactant and the turbulence produced by the fluidized bed conditions, continuous replacement, or saturation, of the aqueous phase by propene is assured for efficient conversion of propene to IPA/IPE. The IPA concentration of the upwardly flowing lighter liquid phase rapidly increases in successive catalytic stages 80-90. This enables a higher proportion of desirable IPE components to be formed under the controlled limited water proportions employed. IPE formation rapidly increases because of higher IPA concentrations and higher temperatures in succeeding stages.

The heavy liquid at the top of reactor stage 90, that is removed from the reactor vessel 78 as recycle water stream S-7 leaving the exit end of reactor vessel 78, contains a small proportion of sulfuric acid produced by desulfonation of the sulfonic acid catalyst. However, recycle of stream S-7 back to the first catalytic reaction stage 80 results in reduction of the desulfonation rate of the sulfonated resin by mass action effect. Furthermore, the close control that is provided over catalyst particle temperature, operation of the catalytic stages at maximum temperatures less than conventional, and assurance of water at each catalyst particle serves to reduce the deactivation rate for a given sulfonated ion exchange resin catalyst. As a consequence, oligomer (higher polymer) formation is limited to values significantly less than the amount of oligomers in produced prior processes.

Overall water to propene molar ratio is a fraction of that employed in present commercial processes. Conventional processes have overall molar ratios of 12:1 to 15:1 water to propene as compared with the exemplary ratio of only 1.56. Unlike the DT process, using a catalyst of the general type employed in the present exemplary process, only the less dense phase from the reactor is further cooled and then subjected to separation in order to segregate the oxygenates from unreacted hydrocarbons. As a consequence, the present process involves a significantly smaller volume of liquid subject to separation procedures to effect recovery of a like amount of oxygenate end product.

Reducing the water recycle rate to a fraction of that employed in prior processes, should cause the catalyst consumption per unit of oxygenated fuel additive produced to be less than ⅓ that required in the Deutsche Texaco process. Loss of sulfonic acid group from the ion exchange catalyst by hydrolysis to the circulating liquid water phase out has been reported to be the primary mechanism of deactivation of the sulfonated catalyst for the DT process. Circulating significantly less water recycle in the present process, coupled with greater assurance of water at the catalyst particle surface and lower maximum catalyst particle temperatures reduces potential hydrolysis activity loss as well as polymer formation. For an acidic, sulfonic resin catalyst, recycling of weak sulfuric acid back to the first stage feed to stage 80 acts to restore any catalyst activity apart from decreasing the loss of sulfonic acid sites by hydrolysis through mass transfer action.

Operation of the initial catalytic stages 80-84 in the present process at lower than conventional bed temperatures after mid-run as in prior propene hydration processes, has been found advantageous because propene conversion to oligomers is restricted to a greater extent than heretofore has been the case, even though the concentration of propene is greatest in the initial stage and there is a significant amount of dilution products present in the less dense phase. In addition, the rate of oligomer formation is significantly decreased. An overall slight increase in catalyst inventory requirements for producing a give oxygenate product in accordance with the present invention, is more than off-set by the higher overall propene conversion percentages realized by practice of the present process.

Better limitation of maximum catalyst particle temperatures, no more than about 290° F. restricts the formation of unwanted oligomers as a result of propene reactant combining with itself or other olefins present. Operation at lower catalyst bed temperatures decreases the desulfonation rate of the ion exchange sulfonic acid catalyst. Limiting oligomer formation decreases the deactivation rate of the catalyst. Significantly higher polymer formation can occur when operating at temperatures of the order of 300° F. This is avoided in the present process.

The use of fluidized catalytic stages in reactor 78 with constant circulation of reactants in each stage makes temperature control in each stage easier to monitor and implement and thereby contributes to an extension of catalyst life.

Partial periodic replacement of catalyst avoids the necessity of replacing the full amount of catalyst in each catalytic stage 80-90. This replenishment of catalyst is accomplished by introducing a quantity of fresh catalyst into final reactor stage 90 through line 191 after opening of valve 193, accompanied by selective opening of the valves 194, 190, 186, 182, 180 and 176. During the time that valves 194, 190, 186, 182, 180 and 176 are open, liquid containing suspended catalyst particles is allowed to flow through respective lines 192, 188, 184, 181, 178 and 174. Thus, a small amount of catalyst is removed from the first bed 80, while catalyst which drains from corresponding second, third, fourth, fifth and sixth catalytic stages 82-90, is redirected into the catalytic bed therebelow. It is contemplated that about 1/50th of the total volume of catalyst in each of the beds 80-90 be removed from the lower bed 8, or transferred to the next lower catalytic stage 82-90, each time the catalyst is replenished in final stage 90, and equal amount of catalyst is transferred to successive stages. Successive introduction of catalyst from the immediately proceeding catalytic stage into each of the catalytic stages, provides the most efficient use of the catalyst, improves its longevity, and permits the process operator to add catalyst to only the upper stage 90.

Viewing FIG. 1B, it is to be noted that the heavy liquid-light liquid interface at the top of reactor vessel 78 is schematically indicated by the scalloped line 196. The composition of the light liquid above the interface line is indicated in the material balance box score as stream S-25; the composition of the heavy liquid below the interface line is represented by the stream S-7 of the box score. As is also evident from the box score of Table I, the composition of the reactants in fluidized beds 80-90 inclusive is set out as S-9, S-12, S-15, S-18, S-21 and S-24 respectively of the material balance box score.

Stream S-25 flowing through line 134, after flowing through successively oriented heat exchangers 68, 112, 116, 120, 124 and 106 passes through air cooler 136 before flowing into light liquid heavy liquid separator 138. In the context of this process, light liquid is the term designating the organic overhead (stream S-25) from reactor vessel 78. Heavy liquid on the other hand is principally water that separates from the organic overhead components which exit from the final catalytic stage 90. The water constituting such liquid is returned to the infeed of the first catalytic stage 80 as stream S-27 via line 208.

Sulfuric acid, being very polar, tends to be preferentially retained in an aqueous medium when two phase separation is permitted. This takes place in the final stage of the reaction zone defined by reactor 78. Liquid phase particulate fluidization is very smooth so that a distinct solid-fluid interface occurs in each fluidized reaction stage 80-90 under the preferred reaction conditions. In the final stage 90, an enlarged diameter space for the fluid separation allows the less dense liquid organic phase to separate from the more dense aqueous liquid phase as indicated by the interface level 196 above the uppermost stage 90 in FIG. 1B. The aqueous phase represented by stream S-7 contains only a very small fraction of the alcohols formed with a negligible proportion of IPE being present. Stream S-7 is returned by pump 200 preferentially to the first stage 80. Although this directionally acts to increase the yield of IPE by allowing more combination of propene with recycled IPA, the formation of IPE is desired for a motor fuel additive because it has a significantly lower Reid vapor pressure (RVP) than IPA while retaining equivalent octane blending characteristics on a volumetric basis when blended with typical refinery gasoline components. The bulk of any sulfuric acid is thus retained and returned to the reaction zone where it acts to prolong activity.

Because of the solubilizing action of the IPA component in the gasoline oxygenate additive produced, more water than usual can be retained by the final gasoline blend without separation of a water phase at a given temperature. Thus, it is possible to achieve the necessary water separation for the oxygenate product when blended for most ASTM Class C or higher refinery gasolines at the requisite 2.0 or 2.7 weight percent oxygen levels by simply cooling the organic phase represented by stream S-25 to a lower temperature and separating the resultant aqueous phase formed utilizing separation section 16 as depicted in FIG. 1C. The material balance give relates to typical summer conditions. This separation would be carried out by light liquid-heavy liquid separator 138 for the air cool product and by light liquid-heavy liquid separator 204 for the water cooled product. The concentration of sulfuric acid found in aqueous stream S-27 should be less than that separated from the recycle stream S-7. Furthermore, the concentration of sulfuric acid found in aqueous stream S-25 should be less than the sulfuric acid content found in stream S-27.

Acid is prevented from being present in stream S-28 which is sent to separation, by virtue of the fact that the resident water forms a minimum boiling point azeotrope with the $C_3$ components, and this water is readily separated because it has limited solubility at reflux conditions. As indicated, sulfuric acid is preferentially soluble in the water rather than the organic constituents. It is to be noted that part of the deionized water makeup could supplement the acid free water returned by pump 248 to light liquid-heavy liquid separator 204, so that neutralization of the oxygenate product is more than reasonably precluded under the process of this invention.

The lighter organic layer from the separator 138 represented by the stream S-26 is principally IPA, IPE, some water vapor, propene, and lesser amounts of propane, ethane and ethylene. That stream, after passing through heat exchanger 207, is introduced into a second light liquid/heavy liquid separator 204, which serves to further separate water from the less dense organic liquid. The separated water identified as stream S-29 is returned to recycle line 208 by a line 212. The light liquid overhead from separator 204 and identified in the box score of Table I as stream S-28, is made up of unreacted hydrocarbon components, $C_3$ alcohols, IPE, minor amounts of other alcohols, acetone, $C_6$ and $C_9$ olefins, and some water, the proportion of which is dependent on the temperature.

The light liquid stream S-28 from separator 204 is first passed through plate heat exchanger 222 and then tube and shell heat exchanger 224, and then introduced into a central part of depropanizer still 218 via line 216. Steam is used for the reboiler in the bottom of depropanizer column 218 through line 228. Trays are employed in column 218 to separate the oxygenate product produced in the present process from unreacted hydrocarbons. It is understood that other vapor-liquid contacting means such as packing could be substituted for the trays. A portion of the hot oxygenate bottoms from depropanizer 218 are diverted to the reboiler of deethanizer 250 through supply and return lines 278. It is to be understood in this respect that other low level heat such as a portion of stream S-25 which by-passes the temperature control heat exchangers 68, 112, 116, 120, 124 and 106 could be substituted as the heat source for the comparatively small deethanizer reboiler duty requirements.

Oxygenate product leaves still 218 via line 230. The composition of oxygenate product-out stream S-30 is set forth in the box score of Table I.

The gaseous overhead from depropanizer 218 flowing through line 234 is directed into the section 238 of drum 232 after passing through heat exchanger 236, where the lighter fraction is sent back to the top of tower 218. The heavier fraction from section 238 is introduced into line 216 for return to light liquid-heavy liquid separator 204 intermediate the upper and lower ends thereof. The gaseous overhead from section 238 is conveyed to section 240 of the reflux drum where the condensed hydrocarbon product is pumped through line 251 for introduction into deethanizer still 250.

A lighter fraction separated from the material flow into section 240 of drum 232 is directed to the central part of deethanizer 250 via line 251 as stream S-31. Dissolved water in the deethanizer feed is separated within vessel 250 and proceeds overhead with the overhead product. Upon condensation, the water is drawn off as a stream flowing through line 272 which is sent back to section 240 of reflux drum 232. Water has only a limited solubility in the liquid hydrocarbon stream returned as reflux to the top of deethanizer 250 through line 270. The net water separated overhead by the depropanizer 218 is sent back to the light liquid-heavy liquid separator 204 in the preferred embodiment or can be returned to the depropanizer 218 as an alternate arrangement. Heat is introduced into the bottom of column 250 by virtue of the fact that a portion of the bottoms from depropanizer 218 are circulated through the heating coils indicated schematically by the dashed lines at the bottom of still 250.

The overhead from column 250 is directed into vapor-liquid reflux drum 262 after having passed through heat exchanger 266. A lighter fraction separated from the end flow to the drum 262 is returned to the top of column 250, while the heavier fraction which is separated in the drum is redirected into the section 240 of reflux drum 232 by line 272. The by-product out as an overhead from drum 262 is designated at stream S-32 in the box score of Table I and consists of ethane, ethylene and a very minor amount of propene. The bottoms from deethanizer 250 are returned as S-2 which joins with fresh feed stream S-1.

One feature of the present invention is the fact that the oxygenate component has 26.096 weight percent oxygen, higher than IPA, because of the water content. The IPA and IPE in admixture also impart to the motor fuel blending agent the capability of dissolving additional amounts of water, even under exposure to cold winter temperatures. Furthermore, because of the low freezing point imported to the gasoline fluid and absence of an aqueous layer phase separation, ice formation is precluded. Dissolved quantities of water act as an octane enhancer in motor fuel, probably because of higher latent heat values that cool the initiating temperature present at spark ignition.

ALTERNATIVE REACTOR SECTION EMBODIMENT

It is to be understood that as an economic process alternative, particularly in those cases where it is necessary to handle a relatively large volume of less dense fluid making up stream S-25 which exits from the reactor 78, it may be advantageous from an equipment standpoint to use a multiplicity of reactor vessels in staged, serial relationship. For example, three reactor vessels could be substituted for the single reactor vessel of FIG. 1B, with each vessel being provided with two catalytic stages. The use of three serially connected, two catalytic stage vessels would enhance more reasonable bed expansions consistent with the design fluids flowing in the particular reactor vessel. For example, the vessel containing the first two fluidized catalytic bed stages could be of a smaller diameter than the vessel containing the third and fourth fluidized bed stages whereas the final vessel containing the fifth and sixth fluidized catalytic stages could have an even larger diameter consistent with the higher fluid volumes for these stages. Catalyst transfer and replenishment between the lowermost stage of a vessel and an earlier stage in a proceeding vessel may be readily accomplished by withdrawing catalyst into a comparatively small volume catalyst transfer vessel, followed by lifting of this vessel to the top of the proceeding vessel. Catalyst would then flow by gravity from this transfer vessel to the uppermost stage of the proceeding vessel. Similarly, fresh or rejuvenated catalyst could be added to the sixth or final stage vessel using a similar lifting procedure. This multiple reactor vessel system would have the advantage of limiting overall vessel height. It also enhances replenishment of catalyst in that catalyst can be added to individual vessels, particularly during initial on stream operation, without the necessity of transferring catalyst from stage to stage each time a catalyst addition is carried out.

I claim:

1. A method of preparing an oxygenate which contains isopropanol, diisopropyl ether and water, and that is useful as an additive for motor fuels, said method comprising the steps of:

providing a $C_3$ hydrocarbon feed stock containing a major proportion of propene;

providing a feed stream containing water;

providing a catalytic reactor zone made up of a number of serially interconnected catalytic stages each having a lower inlet and an upper outlet, and presenting in said serial order thereof, an initial catalytic stage and a final catalytic stage, said stages being located in disposition and interconnected in a manner such that the outlet of each stage is connected to and communicates with the inlet of the next adjacent stage in the serial order thereof.

each stage being provided with a quantity of a particulate strongly acidic ion exchange catalyst characterized by the property of catalyzing the hydrolysis of said feed stock by the water;

introducing a quantity of said feed stock and the water into the inlet of said initial catalytic stage, and into respective inlets of a plurality of catalytic stages serially connected therewith for exothermic reaction of the $C_3$ feed stock with the water;

maintaining the molar ratio of the water to propene delivered to each stage within the range of from about 2:1 to about 6:1;

causing the feed stock and water after introduction thereof into a respective catalytic stage, and the resultant isopropanol and diisopropyl ether formed therefrom, to flow upwardly in serial order through corresponding stages from the outlet of a respective stage to the inlet of the stage next adjacent thereto, with the reactants exiting through the outlet of the final stage of said number thereof;

maintaining the temperature of the reactants in each of the catalytic stages receiving feed stock and water within a range of from about 250° F. to about 300° F., with the pressure in each of the stages receiving feed stock and water being at a level of from about 1200 psia to about 3000 psia;

separating a substantial proportion of the isopropanol, the diisopropyl ether, any unreacted feed stock, and any residual organic components that may have formed in the reactor zone, from at least a proportion of the unreacted water in the outflow from the outlet of the uppermost of said catalytic stages receiving feed stock and water;

removing said proportion of separated water from said uppermost catalytic stage as a stream apart from said isopropanol, the diisopropyl ether, water, unreacted feed stock, and any residual organic components that may have formed in the reactor zone; and separating from said unreacted feed stock an oxygenate motor fuel additive fraction, said oxygenate fuel additive fraction including isopropanol, diisopropyl ether, and water together with any residual organic components that may have formed in the reactor zone.

2. A method of preparing a motor fuel oxygenate additive as set forth in claim 1, wherein is included the step of maintaining the temperature of the reactants in said catalytic stages within a range from about 260° F. to about 295° F.

3. A method of preparing a motor fuel oxygenate additive as set forth in claim 1, wherein is included the step of maintaining the temperature of the reactants in said catalytic stages within a range from about 265° F. to about 290° F.

4. A method of preparing a motor fuel oxygenate additive as set forth in claim 1, wherein is included the step of maintaining the temperature of the reactants in said catalytic stages at temperature levels which successively increase from the lowermost stage receiving feed stock and water to the uppermost of said stages.

5. A method of preparing a motor fuel oxygenate additive as set forth in claim 4, wherein is included the step of limiting the increase in temperature between proximal stages to a value within a range of from about 3° F. to 8° F.

6. A method of preparing a motor fuel oxygenate additive as set forth in claim 1, wherein is included the step of maintaining the pressure in each of said catalytic stages to a value within the range of about 1700 psia to 2200 psia.

7. A method of preparing a motor fuel oxygenate additive as set forth in claim 1, wherein the molar ratio of water to propene introduced into each of the stages is maintained within the range of from about 2.5:1 to about 5:1.

8. A method of preparing a motor fuel oxygenate additive as set forth in claim 1, wherein the ratio of water to propene introduced into the initial stage is maintained within the range of from about 3:1 to about 3.5:1.

9. A method of preparing a motor fuel oxygenate additive as set forth in claim 1, wherein is included the step of providing from about 3 to about 9 of said catalytic stages.

10. A method of preparing a motor fuel oxygenate additive as set forth in claim 1, wherein is included the step of providing from about 4 to about 8 of said catalytic stages 11. A method of preparing a motor fuel oxygenate additive as set forth in claim 1, wherein is included the step of providing 6 of said catalytic stages.

12. A method of preparing a motor fuel oxygenate additive as set forth in claim 1, wherein is included the step of maintaining the reactants in the lowermost stage at a temperature of about 266° F., a second stage next thereabove at a temperature of about 273° F., a third stage next above said second stage at a temperature of about 279° F., a fourth stage next above said third stage at a temperature of about 284° F., a fifth stage next above said fourth stage at a temperature of about 288° F., and a sixth stage next above said fifth stage at a temperature of about 290° F., with the pressure in said stages being from about 1750 to about 2050 psia.

13. A method of preparing a motor fuel oxygenate additive as set forth in claim 1, wherein is included the step of bringing the feed stock and water directed to each catalytic stage, into heat exchange relationship with a medium at a temperature and present in an amount effective to maintain the temperature of the feed stock and water introduced into a respective catalytic stage within said temperature range thereof.

14. A method of preparing a motor fuel oxygenate additive as set forth in claim 1, wherein is included the step of maintaining the particulate catalyst in each of said stages in a condition presenting a fluidized bed for enhancing intimate contact of the catalyst particles with the feed stock and water introduced into a respective catalytic stage.

15. A method of preparing a motor fuel oxygenate additive as set forth in claim 1, wherein is included the step of periodically removing a proportion of the particulate catalyst from the lowermost stage, and concomitantly therewith, directing a similar proportion of catalyst from each stage to the stage there next below to facilitate replacement of catalyst without significantly interfering with operation of the process.

16. A method of preparing a motor fuel oxygenate additive as set forth in claim 1, wherein is included the step of returning the separate stream of water removed from the outflow from the uppermost of said catalytic stages to the lowermost catalytic stage as recycle water.

17. A method of preparing a motor fuel oxygenate additive as set forth in claim 18, wherein is included the step of returning isopropanol contained in the recycle water back to the lowermost catalytic stage.

18. A method of preparing a motor fuel oxygenate additive as set forth in claim 1, wherein said feed stock contains a minor proportion of $C_2$ hydrocarbon constituents and wherein is included the steps of removing said $C_2$ constituents from any unreacted feed stock outflow from the uppermost catalytic stage, and thereafter recycling the recovered propene feed stock back to the catalytic reactor.

19. A method of preparing a motor fuel oxygenate additive as set forth in claim 1, wherein is included the steps of maintaining the temperature of the reactants in the final catalytic stage at a level whereby temperature and pressure conditions exist therein causing the isopropanol, the diisopropyl ether, and any residual organic components that may have formed in the reactor zone to collect in said final stage above and separate from unreacted water as a less dense organic phase therebelow.

20. A method of preparing a motor fuel oxygenate additive as set forth in claim 19, wherein is included the steps of cooling the less dense organic phase which separates from the water in said final catalytic stage, to a level to effect removal of further residual water therein, and recycling the water separated from the more dense water phase, along with said residual water to the reactor zone.

21. A method of preparing a motor fuel oxygenate additive as set forth in claim 20, wherein is included the steps of washing the less dense organic phase from the final light liquid-heavy liquid separator, said washing step includes subjecting the less dense organic phase to water which has been deionized, or using separated water from distillation to insure that the oxygenate motor fuel additive is substantially free of said acid.

22. A method of preparing a motor fuel oxygenate additive as set forth in claim 1, wherein included the step of utilizing the solubilizing action of isopropanol in the oxygenate motor fuel additive to increase the amount of water that may be dissolved in the final motor fuel blend while retaining required compatibility characteristics with the motor fuel with which the additive is added.

* * * * *